(12) United States Patent
Parker

(10) Patent No.: US 8,695,590 B2
(45) Date of Patent: Apr. 15, 2014

(54) ADJUSTABLE STYLET FOR ENDOTRACHEAL TUBE

(75) Inventor: Jeffrey D. Parker, Cincinnati, OH (US)

(73) Assignee: Parker Medical, Inc., Cincinnati, OH (US)

( * ) Notice: Subject to any disclaimer, the term of this patent is extended or adjusted under 35 U.S.C. 154(b) by 1964 days.

(21) Appl. No.: 11/423,595

(22) Filed: Jun. 12, 2006

(65) Prior Publication Data

US 2007/0287961 A1 Dec. 13, 2007

(51) Int. Cl.
*A61M 16/00* (2006.01)
*A62B 9/00* (2006.01)

(52) U.S. Cl.
USPC .................. 128/200.26; 128/207.14

(58) Field of Classification Search
USPC .................. 128/200.24, 200.26, 207.14–17; 600/106; 604/95.04, 164.01, 164.07, 604/165.01, 165.02; 606/108
See application file for complete search history.

(56) References Cited

U.S. PATENT DOCUMENTS

| | | | |
|---|---|---|---|
| 4,150,676 A | | 4/1979 | Jackson |
| 4,329,983 A | | 5/1982 | Fletcher |
| 4,356,821 A | * | 11/1982 | Rind .................. 128/207.14 |
| 4,529,400 A | | 7/1985 | Scholten |
| 4,573,451 A | * | 3/1986 | Bauman .................. 600/190 |
| 4,589,410 A | | 5/1986 | Miller |
| 4,832,019 A | * | 5/1989 | Weinstein et al. ....... 128/207.17 |
| 4,903,995 A | * | 2/1990 | Blenkush et al. .............. 285/38 |
| 5,069,206 A | * | 12/1991 | Crosbie .................. 128/207.17 |
| 5,259,377 A | | 11/1993 | Schroeder |
| 5,490,504 A | * | 2/1996 | Vrona et al. ............. 128/207.17 |
| 5,758,656 A | * | 6/1998 | Schroeder .................. 600/585 |
| 5,791,338 A | * | 8/1998 | Merchant et al. ........ 128/200.26 |
| 6,602,240 B2 | * | 8/2003 | Hermann et al. ............. 604/500 |

OTHER PUBLICATIONS

International Search Report from PCT/US2007/067603, mailed Sep. 27, 2007 (4 pages).
Written Opinion from PCT/US2007/067603, mailed Sep. 27, 2007 (5 pages).

* cited by examiner

*Primary Examiner* — Rachel Young
(74) *Attorney, Agent, or Firm* — Wood, Herron & Evans, LLP

(57) ABSTRACT

A flexible articulating style for an endotracheal tube is provided with a ratchet mechanism whereby to selectively set and maintain a desired curvature of the style, and hence the tube, so that the intubationist may hold the stylet-curved tube with a pencil-like grip at its mid-section for optimal control during intubation.

30 Claims, 5 Drawing Sheets

ADJUSTABLE STYLET FOR ENDOTRACHEAL TUBE

FIELD OF THE INVENTION

The present invention relates to endotracheal tubes, and more particularly, to stylets for endotracheal tubes.

DESCRIPTION OF PRIOR ART

When a patient stops breathing, it is imperative that effective ventilation be instituted as soon as possible. Ventilation is best accomplished by forcing air through an endotracheal tube (also referred to as an orotracheal tube or a nasotracheal tube) inserted through the mouth (or nose) and laryngeal opening and into the trachea. The endotracheal tube is usually a preformed, semi-flexible tubular member having a gas flow lumen extending therethrough. The tube has an arcuate shape imparted to it and is usually placed into the patient with the aid of either a blade laryngoscope or a guiding device (such placement into the trachea being referred to as "endotracheal intubation").

The tube has to be directed into a relatively small target, namely, the opening into the larynx in the back of the throat. In order to have optimal fine control over the forward end of the tube, which helps in properly positioning and inserting the tube end, the intubationist generally holds the tube in its mid-section with a 3-finger (actually two-finger and thumb), pencil-like grip.

The curvature of the anatomy varies from patient to patient. As the tubes are generally made to a standard curvature, it is often necessary to impart a greater bend to the tube than it was given during its manufacture. One typical way to further bend the tube is to insert a malleable stylet, usually made of metal, through the lumen of the tube, and then to bend the stylet to the desired curvature after its insertion into the tube. The stylet, being stronger than the flexible tube, imparts that curvature to the tube during intubation. As the curvature of the tube is maintained by the malleable stylet, the intubationist can use the pencil-like grip of the tube at its mid-section for optimal control. The malleable stylet does have some drawbacks, however. For example, the fixed curvature which it imparts to the tube may be too great to allow the tube to pass down the trachea, which is a straight, tubular, anatomical structure. Thus, the intubation attempt may need to be interrupted, so that the stylet can be removed from the tube, or the stylet and tube can be removed from the throat, for curvature adjustment. Such delays in intubation are undesirable when the need to ventilate the patient is urgent. Further, the rigidity which a malleable stylet imparts to the tube can be quite traumatic to the airway anatomy.

A flexible, articulating stylet, such as shown in U.S. Pat. No. 5,259,377, the disclosure of which is incorporated herein by reference in its entirety, has a pair of elongated, plastic, flexible members, joined at their distal ends, with a collar attached to one of the members and slidably receiving the other member therethrough. A handle or thumb button on the slidable member may be pushed towards the collar causing the slidable member to slide distally through the collar so as to induce an increase in curvature of the slidable member. Due to the flexibility and relationship of the members, easing up on the thumb button results in the slidable member sliding proximally, resulting in a decrease of its curvature. With the flexible, articulating stylet inserted through the tube, the intubationist thus has the ability to continuously vary the curvature as desired for that patient. Thus, the intubation attempt never needs to be delayed or interrupted in order to remove the stylet, or stylet and tube, to readjust the curvature. Further, the danger of trauma to the airway from an excessive, fixed curvature of the tube is greatly diminished, since the curvature may be easily and remotely relaxed at any time by simply reducing the pressure exerted on the thumb button.

While the flexible, articulating stylet offers these and other advantages over malleable stylets, use of the former presents one particular disadvantage. The thumb button must be continuously depressed during intubation in order to maintain the desired curvature. As that structure is located at the rear or proximal end of the tube, the intubationist must typically utilize his/her hand to grip the stylet and tube at the rear section of the tube in a three- or four-finger fist-grip in order to depress the thumb button and curve the tube. Thus, the intubationist cannot utilize the typical and more advantageous pencil-like grip of the tube at its mid-section for intubation, without foregoing the ability to remotely set and maintain the curvature of the tube.

SUMMARY OF THE INVENTION

The present invention provides a flexible, articulating stylet for an endotracheal tube which allows the intubationist to utilize the pencil-like grip of the tube at its mid-section for intubation without sacrificing the ability to maintain a preselected curvature of the tube during intubation. To that end, and in accordance with the principles of the present invention, the collar and the sliding member are provided with a ratchet mechanism by which the degree of curvature may be selectively set and maintained. Thus, as the intubationist pushes the thumb button to slide the slidable member distally, the ratchet mechanism acts to prevent the slidable member from sliding back proximally, such that the level of curvature may be set and maintained. With the curvature set and maintained by the ratchet mechanism, the intubationist not need hold the rear end of the stylet or of the tube in an awkward, ill-positioned, fist-grip, but may instead manipulate the endotracheal tube with the advantageous pencil-like grip of the tube at its mid-section. Further, the tube curvature, set and maintained by means of the stylet's ratchet mechanism, is quickly and remotely releasable, thereby allowing the tube, which has been highly curved by the stylet in order to traverse the curved airway path into the throat, to straighten out and pass easily and non-traumatically down the straight trachea after the tube has passed through the larynx. The stylet need not be removed during intubation, as is so frequently necessary with malleable stylets. The ratchet mechanism thus takes advantage of the flexibility and remote operation of the articulating stylet features, without foregoing the curvature-holding previously afforded by malleable stylets.

The set curvature can be selectively increased, such as by further pressing the thumb button to cause the slidable member to slide further distally, thereby inducing greater curvature. To reduce or eliminate the curvature, the ratchet mechanism can be released, such that the slidable member no longer has as much, or any, curvature.

The ratchet mechanism may be in the form of ratchet teeth on the slidable member, which interact with an edge(s) of a slot in the collar through which the slidable member is slidably received. The ratchet teeth and/or slot edge(s) are advantageously cammed to facilitate distal sliding of the slidable member. The ratchet teeth and slot edges cooperate to resist proximal sliding of the slidable member. The slot is dimensioned to normally hold the slidable member therein, but has a notch communicating therewith into which the slidable member may pass to release the ratchet mechanism, whereupon the set curvature is released.

By virtue of the foregoing, there is thus provided a flexible, articulating stylet for an endotracheal tube which allows the intubationist to utilize the pencil-like grip of the tube at its mid-section for intubation without sacrificing the ability to maintain a pre-selected curvature of the tube during intubation. These and other objects and advantages of the present invention shall be made apparent from the accompanying drawings and the description thereof.

BRIEF DESCRIPTION OF THE DRAWINGS

The accompanying drawings, which are incorporated in and constitute a part of this specification, illustrate embodiments of the invention, and together with the general description of the invention given above, and the detailed description of the embodiments given below, serve to explain the principles of the present invention.

DETAILED DESCRIPTION OF THE DRAWINGS

Figure 1:
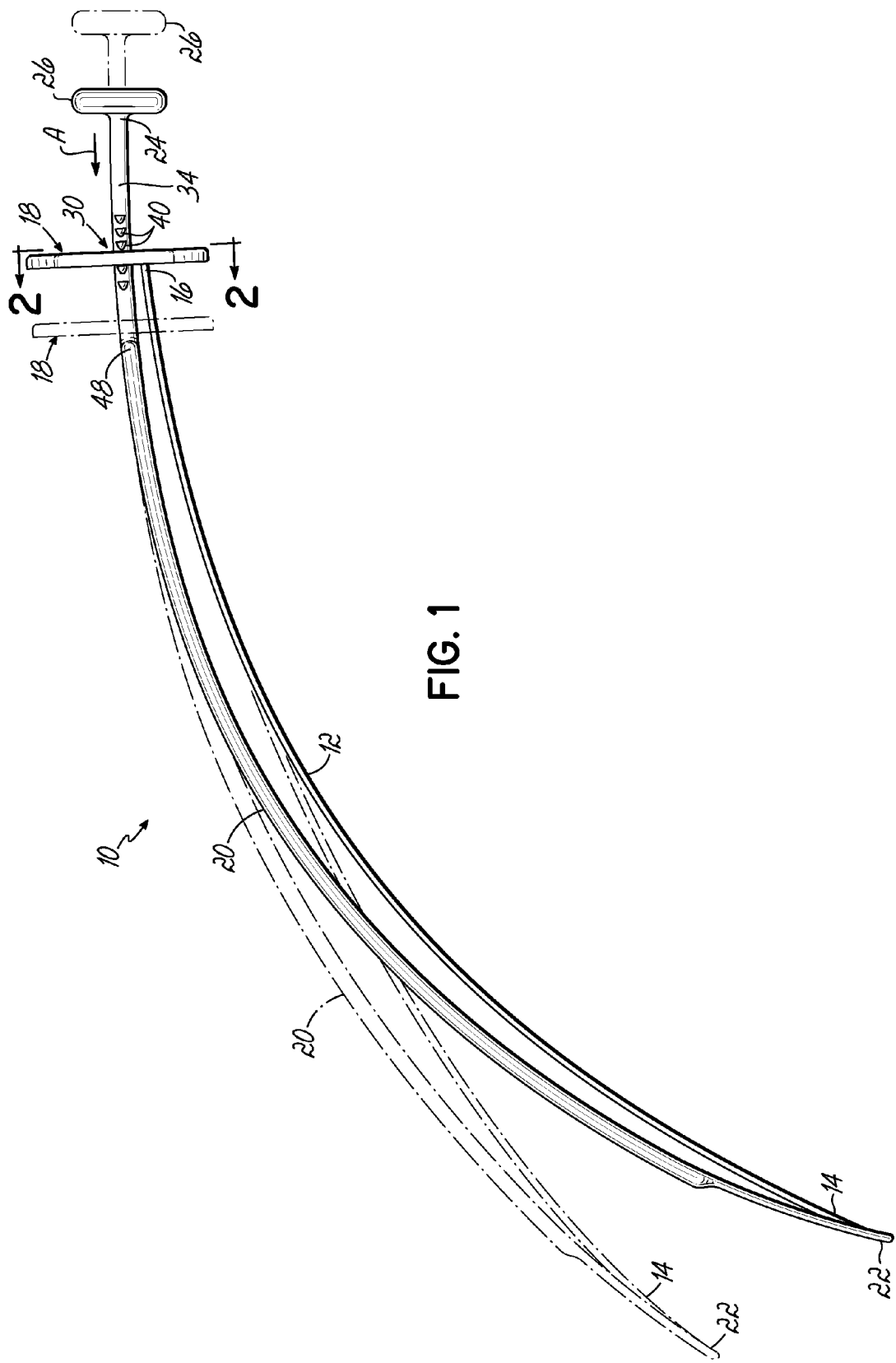
FIG. 1 is a side view of an embodiment of a flexible, articulating stylet with a ratchet mechanism in accordance with the principles of the present invention.

With reference to FIG. 1, there is shown an exemplary flexible, articulating stylet 10 constructed in accordance with the principles of the present invention. Stylet 10 has a string-like or filament-like elongated flexible member 12 having a distal end 14 and a proximal end 16, to which is attached a collar 18. Stylet 10 also has another elongated, flexible member 20 with a distal end 22 and a proximal end 24, to which is attached a thumb button 26. Distal end 14 of member 12 is joined to distal end 22 of member 20 where their paths converge.

Member 20 is normally slidably received through collar 18 such that distal sliding of member 20 (in the direction of arrow A in FIG. 1) induces an increase in curvature thereof (from that shown in dashed line to that shown in solid line in FIG. 1), whereas proximal sliding of member 20 (in the direction opposite of arrow A) reduces that curvature. In accordance with the principles of the present invention, stylet 10 is provided with a ratchet mechanism 30 (FIGS. 2 and 3) as will be described in greater detail hereinbelow by which to selectively set the curvature of member 20.

Figure 2:
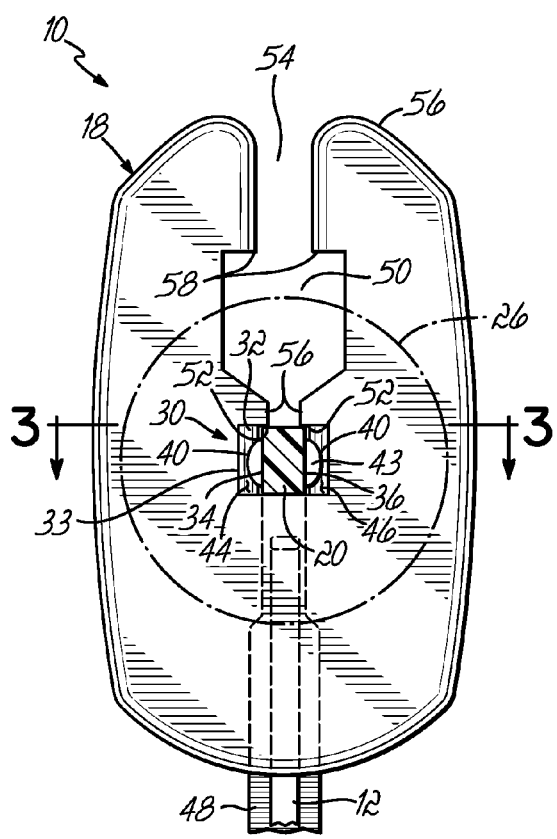
FIG. 2 is a view taken along lines 2-2 of FIG. 1.
Figure 3:
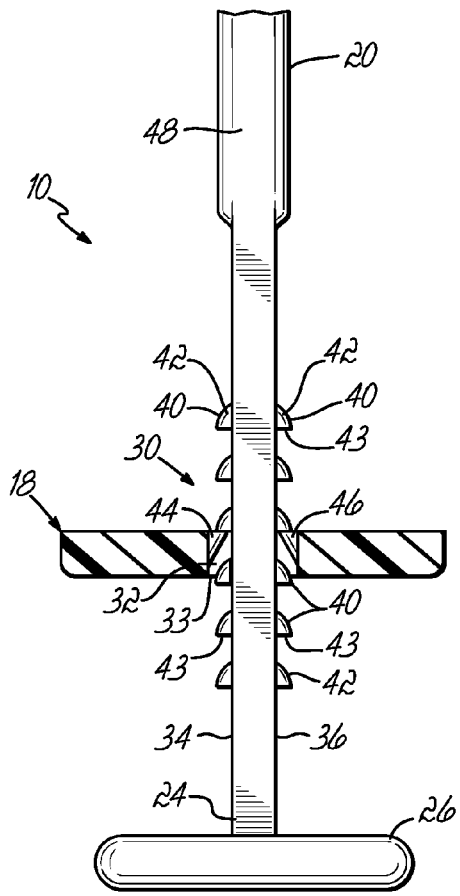
FIG. 3 is a view taken along lines 3-3 of FIG. 2.

With reference to FIGS. 2 and 3, collar 18 includes a slot 32 through which member 20 is normally slidably received. Formed on opposite surfaces 34, 36 of member 20 adjacent its proximal end 24, and spaced longitudinally there along, are a plurality of ratchet teeth 40, each of which may be cammed as at distal-facing surface 42 thereof and have a generally flat, planar proximal face as at 43 thereof. The proximal aspect 33 of slot 32 is wide enough to receive teeth 40 therethrough (as seen in FIG. 3). A pair of opposed slot edges 44, 46 confront respective surfaces 34, 36 of member 20. The edges 44 and 46 are each distally located and advantageously cammed in the proximal facing direction so as to narrow slot 32 there along as seen in FIGS. 2 and 3. Ratchet teeth 40 and one or both of edges 44, 46 cooperate to define ratchet mechanism 30. To that end, collar 18 may be situated between thickened section 48 of member 20 and teeth 40 thereof. Thickened section 48 is larger than slot 32 and so limits proximal sliding of member 20 through slot 32. With collar 18 so-positioned, pushing distally (Arrow A in FIG. 1) on thumb button 26 shortens the distance between button 26 and collar 18 by causing member 20 to slide in the distal direction. As member 20 slides in the distal direction, the distal cammed surface 42 of one or more of teeth 40 selectively pass through slot 32 and past edge(s) 44 and/or 46. As a tooth 40 (or a pair of opposed teeth 40) pass edge(s) 44 and/or 46, slidable member 20 is induced to increase its curvature. Flat aspects 43 of teeth 40 bear against edge(s) 44 and/or 46 such that teeth 40 that have passed the edge(s) cannot readily pass back proximally into or through slot 32. Slidable member 20 thus cannot readily slide in the proximal direction and release or reduce its curvature. Consequently, the distance between thumb button 26 and collar 18, and hence the curvature of member 20, becomes set.

Figure 5:
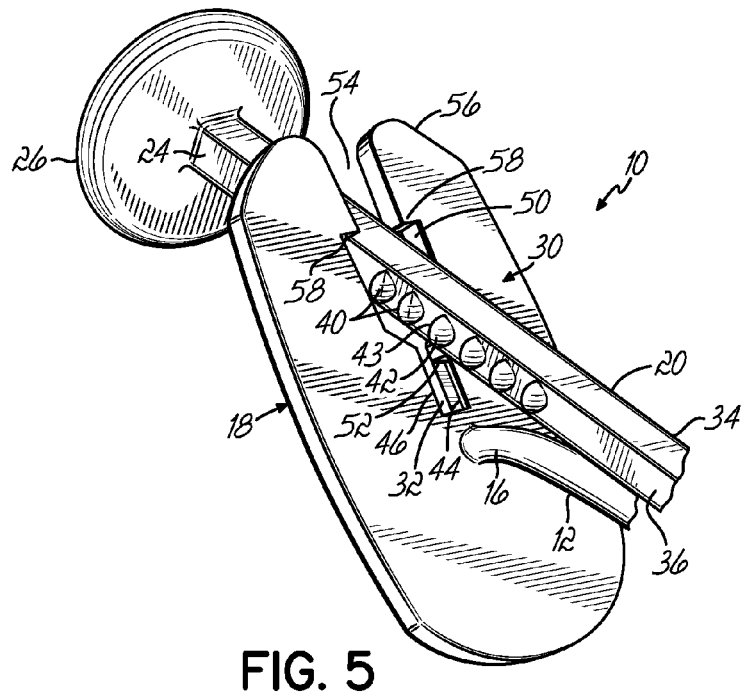
FIG. 5 is a bottom perspective view, of the proximal portion of the stylet of FIG. 1 for purposes of explaining release of the ratchet mechanism thereof.
Figure 4A:
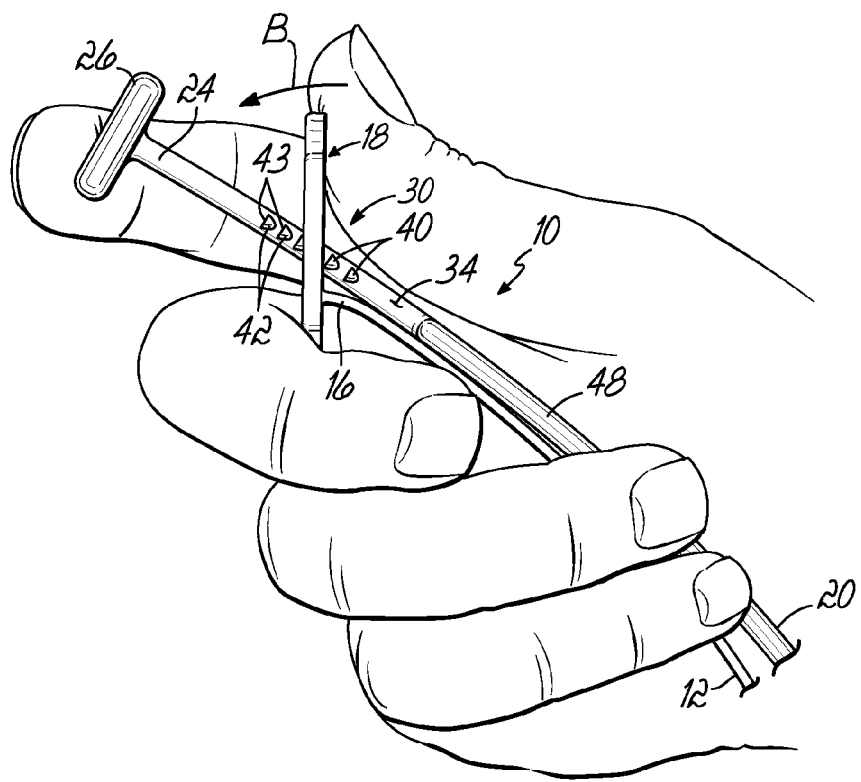
FIGS. 4A and 4B are side views.
Figure 4B:
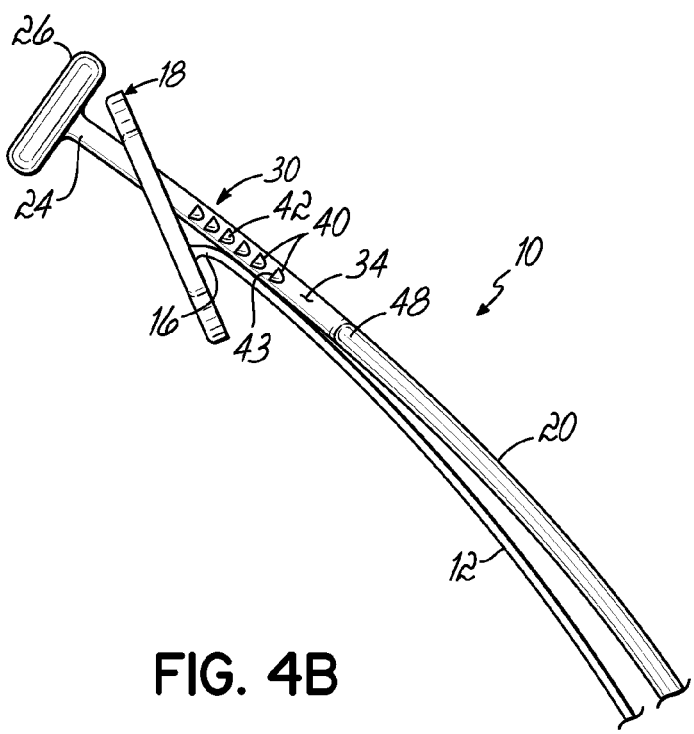

Collar 18 includes a notch 50 communicating with slot 32 and sized so that teeth 40 can pass distally or proximally therethrough. Member 20 may be driven into notch 50, such as beyond shoulders 52 which normally hold member 20 within slot 32. Once within notch 50, the ratchet mechanism 30 is released such that member 20 is free to slide proximally, thereby reducing or eliminating the set curvature thereof. An accessway 54 extends through a lateral edge 56 of collar 18 and through which member 20 may be completely removed from collar 18. To that end, collar 18 may be flipped proximally (in the direction of arrow B in FIG. 4A) so as to drive member from slot 32, where the curvature thereof may have been selectively set, at least into notch 50 as seen in FIGS. 4B and 5 so as to relieve the curvature that had been induced in member 20. Further proximal flipping of collar 18 will drive member 20 all the way into, and ultimately through, accessway 54 so as to completely remove member 20 from collar 18.

Figure 6:
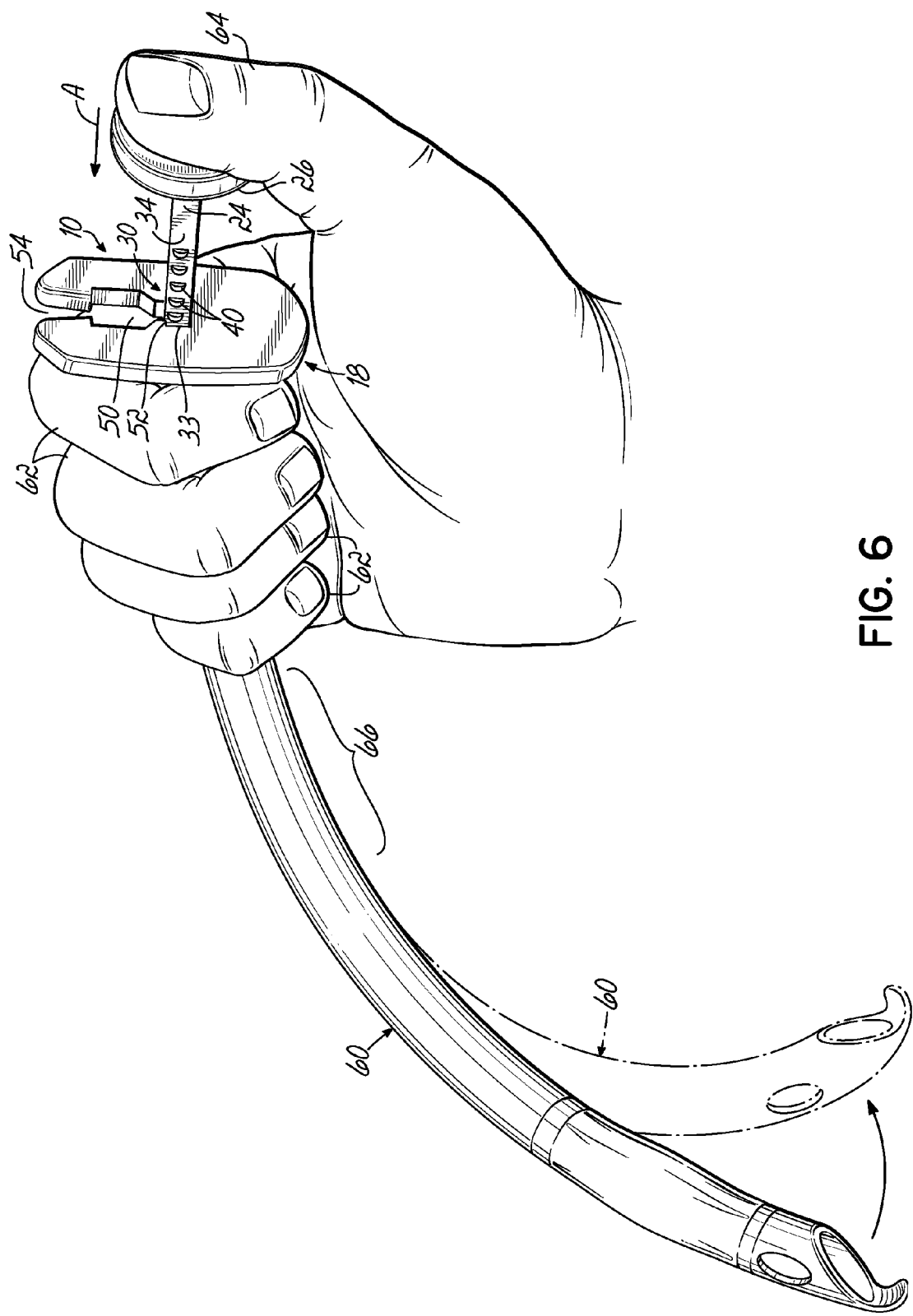
FIG. 6 is a perspective view of an endotracheal tube with the stylet of FIG. 1.
Figure 7:
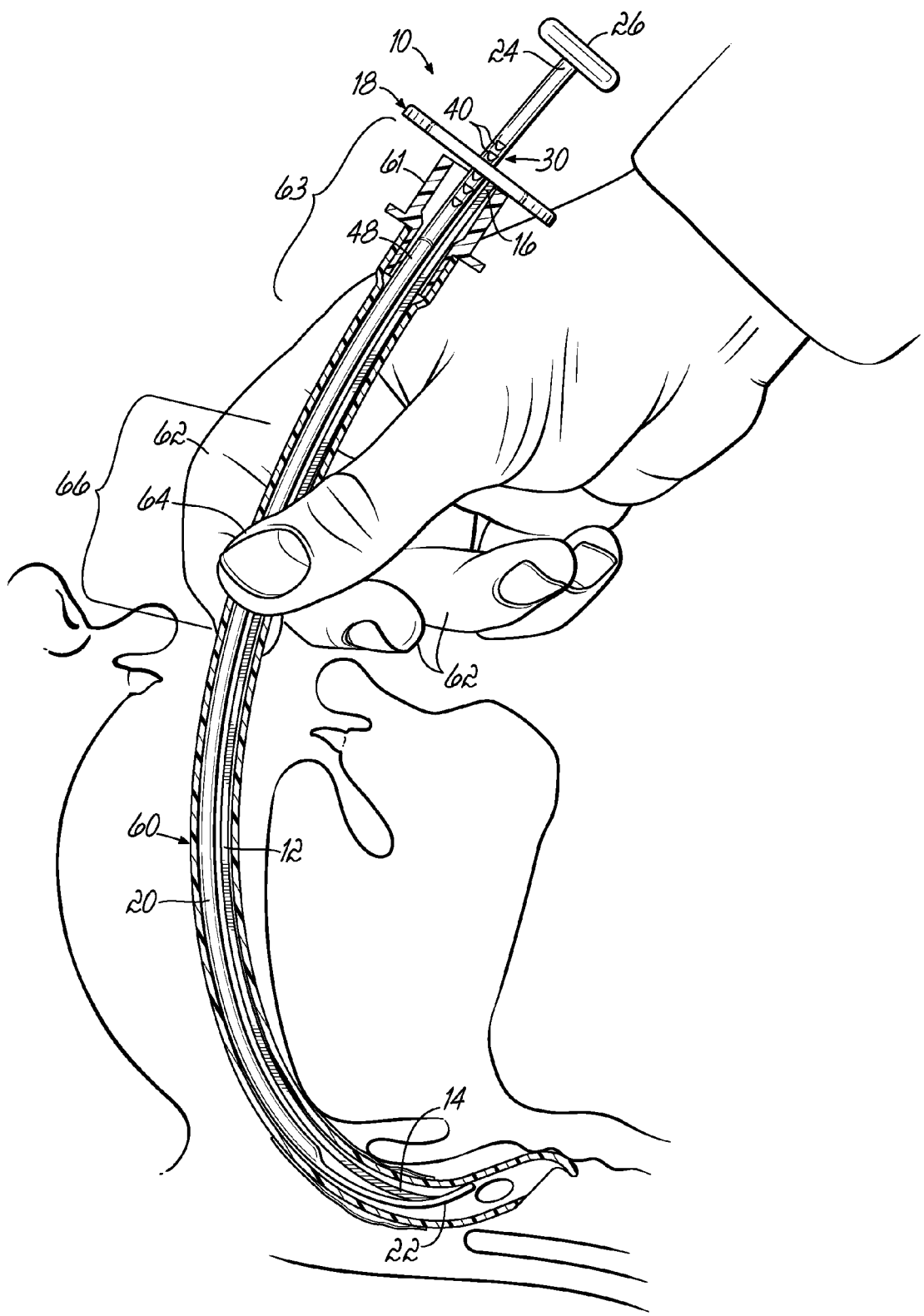
FIG. 7 is a cross-sectional view of the endotracheal tube and stylet of FIG. 2 showing a patient being intubated therewith for purposes of explaining the principles of the present invention.

In use, and with reference to FIGS. 6 and 7, stylet 10 is inserted, distal ends 14 and 22 first, into endotracheal tube 60, such as through connector 61 associated with proximal end 63 thereof (FIG. 7). Thumb button 26 is then pushed distally, such as by the intubationist holding the proximal end 63 of tube 60 with three or four fingers 62 wrapped therearound in a fist-grip just distal to collar 18, and pushing on thumb button 26 with the thumb 64 in the direction of Arrow A, until the desired number of teeth 40 have passed along edge(s) 44 and/or 46 (see FIG. 3) to induce the desired amount of curvature in stylet 10, and hence tube 60 (as shown by comparing the solid line and dashed line of FIG. 6). The intubationist may then take hold of tube 60 with two of fingers 62 and thumb 64 in a pencil-like grip of the tube mid-section 66 as seen in FIG. 7 and proceed with the intubation as conventional, but with the curvature already set. If more curvature is needed, the intubationist merely pushes thumb button 26 further distally to pass more teeth 40 beyond edge(s) 44 and/or 46 thereby inducing greater curvature. If less curvature is desired, collar 18 may be flipped proximally to drive member 20 into notch 50 (FIGS. 4A and 4B), to relieve the curvature, and member 20 may be reloaded into slot 32 and thumb button 26 pressed distally to set a new curvature as desired. Note that, for ease of illustration, not all of the features of a typical endotracheal tube have been shown; such details are shown in my U.S. Pat. No. 5,873,362, the disclosure of which is incorporated herein by reference in its entirety.

By virtue of the foregoing, there is thus provided a flexible, articulating stylet for an endotracheal tube which allows the intubationist to utilize the pencil-like grip of the tube at its mid-section for intubation without sacrificing the ability to maintain a pre-selected curvature of the tube during intubation. The intubationist may also quickly and remotely release the curvature of the stylet and tube, so that the tube may pass easily and non-traumatically down the straight trachea without the necessity of pausing to remove the stylet from the tube.

While the present invention has been illustrated by the description of an embodiment thereof, and while the embodiment has been described in considerable detail, it is not intended to restrict or in any way limit the scope of the appended claims to such detail. Additional advantages and modifications will readily appear to those skilled in the art. For example, ratchet teeth 40 could be provided on only one of surfaces 34 and/or 36. Further, while edges 44 and/or 46 are shown extending into slot 32, they could be the edge openings of slot 32, such that teeth 40 do not otherwise readily pass into slot 32 as shown hereinabove. Additionally, stylet 10 is advantageously molded from plastic as a unitary piece. Members 12 and 20 are thus advantageously plastic. However, they need not be so molded, and member 12 could, for example, be a string or other filament, which need not be plastic. Still further, while member 20 is shown as the slidable member and has its curvature affected to thereby set the curvature of stylet 10, member 12 could alternatively or additionally have its curvature affected to thereby set the curvature of stylet 10. Also, while collar 18 is shown as attached at proximal end 16, it could be located elsewhere on member 12. Similarly, thumb button 26 could be spaced distally of proximal end 24. The invention in its broader aspects is, therefore, not limited to the specific details, representative apparatus and method, and illustrative examples shown and described. Accordingly, departures may be made from such details without departing from the spirit or scope of the general inventive concept.

Having described the invention, what is claimed is:

1. A stylet for selectively varying curvature of an endotracheal tube into which the stylet is received, the stylet comprising:
    a pair of elongated, flexible members each having a distal end and a proximal end, the members being joined together adjacent their distal ends;
    a collar associated with a first of the pair of members, the collar having a slot therethrough, a second of the pair of members being slidably received through the collar slot, such that distal sliding of the second member induces an increase in curvature thereof; and
    a ratchet mechanism associated with the second member and the collar whereby to selectively set the curvature.

2. The stylet of claim 1, the collar including a notch communicating with the collar slot and into which the second member may be moved to release the ratchet mechanism.

3. The stylet of claim 2 further comprising a shoulder between the collar slot and the notch whereby to normally hold the second member in the slot.

4. The stylet of claim 3 further comprising an accessway communicating through a lateral edge of the collar into the notch and through which the second member may be removed from the collar.

5. The stylet of claim 2 further comprising an accessway communicating through a lateral edge of the collar into the notch and through which the second member may be removed from the collar.

6. The stylet of claim 1, the ratchet mechanism including a plurality of ratchet teeth formed on the second member.

7. The stylet of claim 6, the ratchet mechanism including an edge of the slot with which the ratchet teeth interact to set the curvature.

8. The stylet of claim 1, the ratchet mechanism including an edge of the slot.

9. The stylet of claim 8, the edge extending into the slot.

10. The stylet of claim 1 further comprising a thumb button associated with the proximal end of the second member whereby to facilitate the distal sliding of the second member through the slot.

11. The stylet of claim 1, the elongated members being plastic.

12. The stylet of claim 1, the collar being associated with the proximal end of the first member.

13. The stylet of claim 1, the second member having a thickened portion spaced distal of the ratchet mechanism and sized so as not to be slidable through the collar slot, whereby to limit proximal sliding of the second member therethrough.

14. A stylet for selectively varying curvature of an endotracheal tube into which the stylet is received, the stylet comprising:
    a pair of elongated, flexible members each having a distal end and a proximal end, the members being joined together adjacent their distal ends;
    a collar associated with a first of the pair of members, the collar having a slot therethrough, a second of the pair of members being slidably received through the collar slot, such that distal sliding of the second member induces an increase in curvature thereof; and
    a plurality of ratchet teeth spaced longitudinally along a surface of the second member;
    an edge of the collar confronting the surface of the second member and cooperating with the ratchet teeth thereof whereby to selectively set the curvature of the first member.

15. The stylet of claim 14, the ratchet teeth being cammed.

16. The stylet of claim 15, the slot edge being cammed.

17. The stylet of claim 14, the slot edge being cammed.

18. The stylet of claim 14 the plurality of ratchet teeth being spaced longitudinally along opposed surfaces of the second member, and the collar including opposed edges confronting respective ones of the opposed surfaces of the second member.

19. The stylet of claim 18, the ratchet teeth being cammed.

20. The stylet of claim 19, the slot edges being cammed.

21. The stylet of claim 18, the slot edges being cammed.

22. The stylet of claim 18, the slot edges extending into the slot.

23. The stylet of claim 14, the collar being associated with the proximal end of the first member.

24. A stylet for varying curvature of an endotracheal tube into which the stylet is received, the stylet comprising:
    a first elongated member being having a proximal end and a distal end;
    a second elongated member having a proximal end and a distal end, the distal end of the second elongated member being attached adjacent the distal end of the first elongated member;
    a thumb button associated with the second elongated member;
    a collar associated with the first elongated member and having a slot for reciprocally receiving a portion of the second elongated member therethrough with the thumb button and collar being spaced apart by a distance, such that varying the distance by reciprocating the second elongated member through the slot varies curvature induced in at least one of the first and second elongated members; and ratchet teeth formed on the second elongated member and adapted to cooperate with the collar slot whereby to permit selectively fixing the distance to hold a desired curvature.

25. The stylet of claim 24, the collar being associated with the proximal end of the first elongated member.

26. The stylet of claim 25, the thumb button being associated with the proximal end of the second elongated member.

27. The stylet of claim 24, the thumb button being associated with the proximal end of the second elongated member.

28. The stylet of claim 27, the ratchet teeth being distal of the thumb button.

29. The stylet of claim 24, the ratchet teeth being distal of the thumb button.

30. The stylet of claim 24, the collar including a notch communicating with the slot sized to allow the second elongated member portion to pass out of the slot, whereby to release the selectively fixed distance.

* * * * *